(12) United States Patent
Shinoda et al.

(10) Patent No.: US 11,815,581 B2
(45) Date of Patent: *Nov. 14, 2023

(54) MEDICAL INFORMATION PROCESSING APPARATUS, MAGNETIC RESONANCE IMAGING APPARATUS, AND MEDICAL INFORMATION PROCESSING METHOD

(71) Applicant: CANON MEDICAL SYSTEMS CORPORATION, Otawara (JP)

(72) Inventors: Kensuke Shinoda, Otawara (JP); Kazuto Nakabayashi, Nasushiobara (JP); Hitoshi Kanazawa, Utsunomiya (JP); Kazuya Okamoto, Saitama (JP); Hiroshi Takai, Nasushiobara (JP); Nobuyuki Konuma, Utsunomiya (JP); Yuichi Yamashita, Ota-ku (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/734,351

(22) Filed: May 2, 2022

(65) Prior Publication Data
US 2022/0260659 A1  Aug. 18, 2022

Related U.S. Application Data

(63) Continuation of application No. 16/774,116, filed on Jan. 28, 2020, now Pat. No. 11,415,656.

(30) Foreign Application Priority Data

Jan. 30, 2019 (JP) .................. 2019-014140
Jan. 23, 2020 (JP) .................. 2020-009470

(51) Int. Cl.
*G01R 33/56* (2006.01)
*G06T 5/00* (2006.01)
(Continued)

(52) U.S. Cl.
CPC .......... *G01R 33/5608* (2013.01); *A61B 5/055* (2013.01); *A61B 5/7203* (2013.01);
(Continued)

(58) Field of Classification Search
None
See application file for complete search history.

(56) References Cited

U.S. PATENT DOCUMENTS 7,020,318 B2  3/2006 Oshio et al.
9,569,843 B1  2/2017 Mailhe et al.
(Continued)

FOREIGN PATENT DOCUMENTS

CN  101101325 A  1/2008
EP  3 410 392 A1  12/2018
(Continued)

OTHER PUBLICATIONS

Kidoh, M, et al., "Deep Learning Based Noise Reduction for Brain MR Imaging : Tests on Phantoms and Healthy Volunteers", Magnetic Resonance in Medical Sciences, 2019.
(Continued)

*Primary Examiner* — Samah A Beg
(74) *Attorney, Agent, or Firm* — Oblon, McClelland, Maier & Neustadt, L.L.P.

(57) ABSTRACT

A medical image processing apparatus of embodiments includes processing circuitry. The processing circuitry is configured to acquire a data and a g-factor map. The data is generated as a result of a reception by an RF coil. The processing circuitry is configured to determine strength of denoise performed on the data on the basis of the g-factor map and perform the denoise on the data.

13 Claims, 9 Drawing Sheets

(51) Int. Cl.
*G06T 5/50* (2006.01)
*A61B 5/055* (2006.01)
*A61B 5/00* (2006.01)
*G06T 7/00* (2017.01)

(52) U.S. Cl.
CPC ............... *G06T 5/002* (2013.01); *G06T 5/50* (2013.01); *G06T 7/0012* (2013.01); *G06T 2207/10088* (2013.01); *G06T 2207/30004* (2013.01)

(56) References Cited

U.S. PATENT DOCUMENTS

| | | |
|---|---|---|
| 2008/0310695 A1 | 12/2008 | Garnier et al. |
| 2014/0361770 A1 | 12/2014 | Dannels |
| 2017/0124707 A1 | 5/2017 | Sugiura et al. |
| 2018/0349759 A1 | 12/2018 | Isogawa et al. |

FOREIGN PATENT DOCUMENTS

| | | |
|---|---|---|
| JP | 2013-46833 A | 3/2013 |
| JP | 2016-93494 A | 5/2016 |
| JP | 2018-206382 A | 12/2018 |
| WO | WO 2009/128213 A1 | 10/2019 |

OTHER PUBLICATIONS

Sathya Vjayakumar et al. "g-Factor and Gradient Weighted Denoising With Edge Restoration (g-Denoiser) for SENSE Reconstructed MR Images" 2008 5$^{th}$ IEEE International Symposium on Biomedical Imagining: From Nano to Macro. IEEE, 2008.

Kinam Kwon et al. "Multi-Contrast MR Image Denoising for Parallel Imaging Using Multilayer Perceptron." International Journal of Imaging Systems and Technology 26.1 (2016): 65-75. (Year: 2016).

Office Action dated May 16, 2023, in corresponding Japanese Patent Application No. 2020-009470, 4 pages.

MEDICAL INFORMATION PROCESSING APPARATUS, MAGNETIC RESONANCE IMAGING APPARATUS, AND MEDICAL INFORMATION PROCESSING METHOD

CROSS-REFERENCE TO RELATED APPLICATIONS

The present application is a continuation application of U.S. application Ser. No. 16/774,116, filed Jan. 28, 2020, which claims priority to Japanese Patent Application No. 2019-014140, filed on Jan. 30, 2019, and Japanese Patent Application No. 2020-009470, filed on Jan. 23, 2020. The contents of the above-identified applications are incorporated herein by reference in their entirety.

FIELD

Embodiments of the present invention relate to a medical information processing apparatus, a magnetic resonance imaging apparatus, and a medical information processing method.

BACKGROUND

Various manners of denoise for medical images have been proposed, and there is a technique of providing an image obtained by combining an image before denoise and an image after the denoise as an image used for diagnosis.

DETAILED DESCRIPTION

According to one embodiment, a medical image processing apparatus includes processing circuitry. The processing circuitry is configured to acquire a data and a g-factor map. The data is generated as a result of a reception by an RF (Radio Frequency) coil. The processing circuitry is configured to determine strength of denoise performed on the data on the basis of the g-factor map and perform the denoise on the data.

Hereinafter, embodiments of a medical information processing apparatus, a magnetic resonance imaging apparatus, and a medical information processing method will be described in detail with reference to the drawings.

First Embodiment

Figure 1:
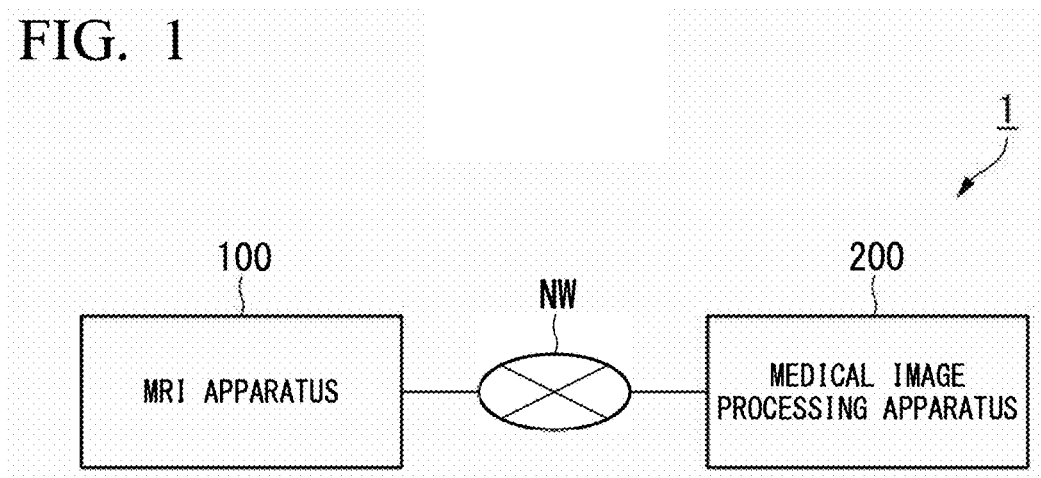
FIG. 1 is a diagram showing an example of a configuration of a medical image processing system according to a first embodiment.

FIG. 1 is a diagram showing an example of a configuration of a medical image processing system 1 according to a first embodiment. For example, the medical image processing system 1 may include a magnetic resonance imaging (MRI) apparatus 100 and a medical image processing apparatus 200, as shown in FIG. 1. The MRI apparatus 100 and the medical image processing apparatus 200 are connected through a network NW. For example, the network NW may include a wide area network (WAN), a local area network (LAN), the Internet, a dedicated line, a wireless base station, a provider, and the like.

The MRI apparatus 100 is an apparatus that generates a medical image (MR image) by applying magnetic fields to an examination object (e.g., a human body), receiving electromagnetic waves generated from hydrogen nuclei in the examination object according to nuclear magnetic resonance using a coil and reconstructing a signal based on the received electromagnetic waves, for example.

The medical image processing apparatus 200 is realized by one or a plurality of processors. For example, the medical image processing apparatus 200 may be a computer included in a cloud computing system or a computer (stand-alone computer) operating alone without depending on other apparatuses. The medical image processing apparatus 200 is an example of a "medical information processing apparatus."

Configuration Example of MRI Apparatus

Figure 2:
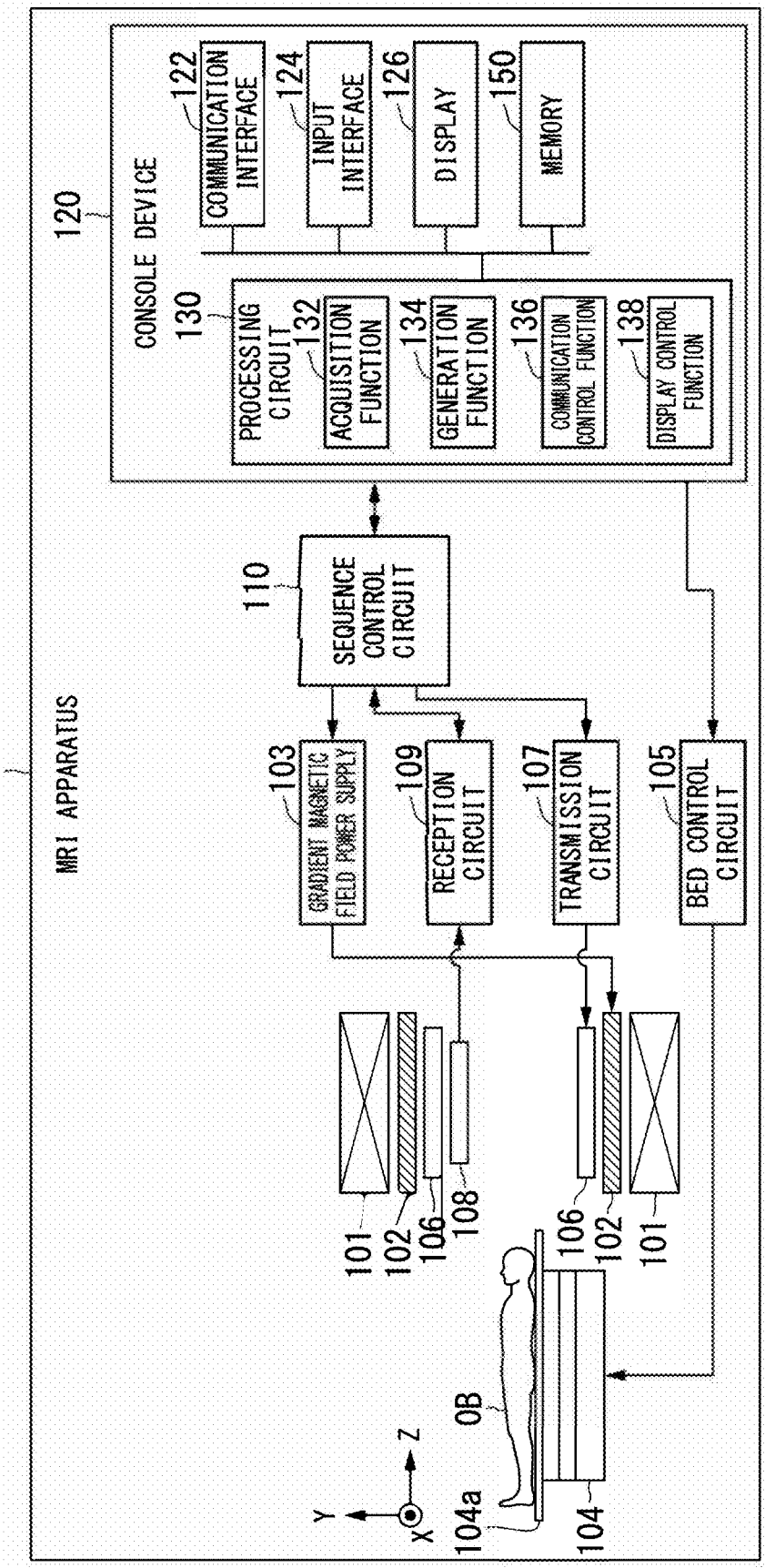
FIG. 2 is a diagram showing an example of an MRI apparatus according to the first embodiment.

FIG. 2 is a diagram showing an example of the MRI apparatus 100 according to the first embodiment. As shown in FIG. 2, the MRI apparatus 100 includes a static magnetic field magnet 101, a gradient magnetic field coil 102, a gradient magnetic field power supply 103, a bed 104, a bed control circuit 105, a transmission coil 106, a transmission circuit 107, a reception coil 108, a reception circuit 109, a sequence control circuit 110, and a console device 120. The transmission coil 106 and the reception coil 108 are an example of "RF coils (radio frequency coils)."

The static magnetic field magnet 101 is a magnet formed in an approximately cylindrical hollow shape and generates uniform static magnetic fields in the internal space thereof. For example, the static magnetic field magnet 101 may be a permanent magnet, a superconducting magnet, or the like. The gradient magnetic field coil 102 is a coil formed in an approximately cylindrical hollow shape and disposed inside the static magnetic field magnet 101. The gradient magnetic field coil 102 is formed by combining three coils corresponding to x, y and z axes perpendicular to one another. A z-axis direction represents a longitudinal direction of a top board 104a of the bed 104, an x-axis direction represents an axial direction perpendicular to the z-axis direction and parallel to the floor of the room where the MRI apparatus 100 is installed, and a y-axis direction represents an axial direction that is a vertical direction with respect to the floor. The three coils corresponding to the respective axial directions individually receive a current from the gradient magnetic field power supply 103 and generate gradient magnetic fields having magnetic field strength varying in accordance with the x, y and z axes. Meanwhile, the z-axis direction is defined as the same direction as static magnetic fields.

The gradient magnetic field power supply 103 supplies a current to the gradient magnetic field coil 102. Here, gradient magnetic fields of the x, y and z axes generated by the gradient magnetic field coil 102 may respectively correspond to a slice selection gradient magnetic field Gs, a phase encoding gradient magnetic field Ge, and a lead-out gradient magnetic field Gr, for example. The slice selection gradient magnetic field Gs is used to arbitrarily determine a cross section to be imaged. The phase encoding gradient magnetic field Ge is used to change the phase of a magnetic resonance signal depending on a spatial position. The lead-out gradient magnetic field Gr is used to change the frequency of a magnetic resonance signal depending on a spatial position.

The bed 104 includes the top board 104a on which an examination object OB is placed. The top board 104a of the bed 104 on which the examination object OB is placed is inserted into a hollow (imaging hole) of the gradient magnetic field coil 102 under the control of the bed control circuit 105. In general, the bed 104 is installed such that the longitudinal direction thereof is parallel to the central axis of the static magnetic field magnet 101. The bed control circuit 105 drives the bed 104 such that the top board 104a moves in the longitudinal direction and the vertical direction under the control of the console device 120.

The transmission coil 106 may be provided inside the gradient magnetic field coil 102, for example. The transmission coil 106 may be a coil for a whole body (whole body coil) accommodated in a frame including the static magnetic field magnet 101, for example. The transmission coil 106 receives a supply of a current from the transmission circuit 107 and generates radio frequency magnetic fields (hereinafter referred to as radio frequency (RF) pulses) for exciting nuclear spin in the examination object OB. Meanwhile, the transmission coil 106 may be a local coil provided near the body surface of the examination object OB instead of the whole body coil.

The transmission circuit 107 supplies the transmission coil 106 with a current corresponding to a Larmor frequency determined by the type of a nucleus that is a target and a magnetic field strength to the RF coil 108 and generates RF pulses form the transmission coil 106.

The reception coil 108 is provided inside the gradient magnetic field coil 102 and receives a magnetic resonance signal generated from the examination object OB according to the influence of RF pulses. The magnetic resonance signal includes, for example, a signal intensity component and a phase component. When the reception coil 108 receives the magnetic resonance signal, the reception coil 108 outputs the received magnetic resonance signal to the reception circuit 109. The reception coil 108 may be realized by a phased array coil having at least two coil elements arranged in an array form. Meanwhile, the reception coil 108 is not limited to the phased array coil and may be realized by a single RF coil for both transmission and reception.

Figure 3:
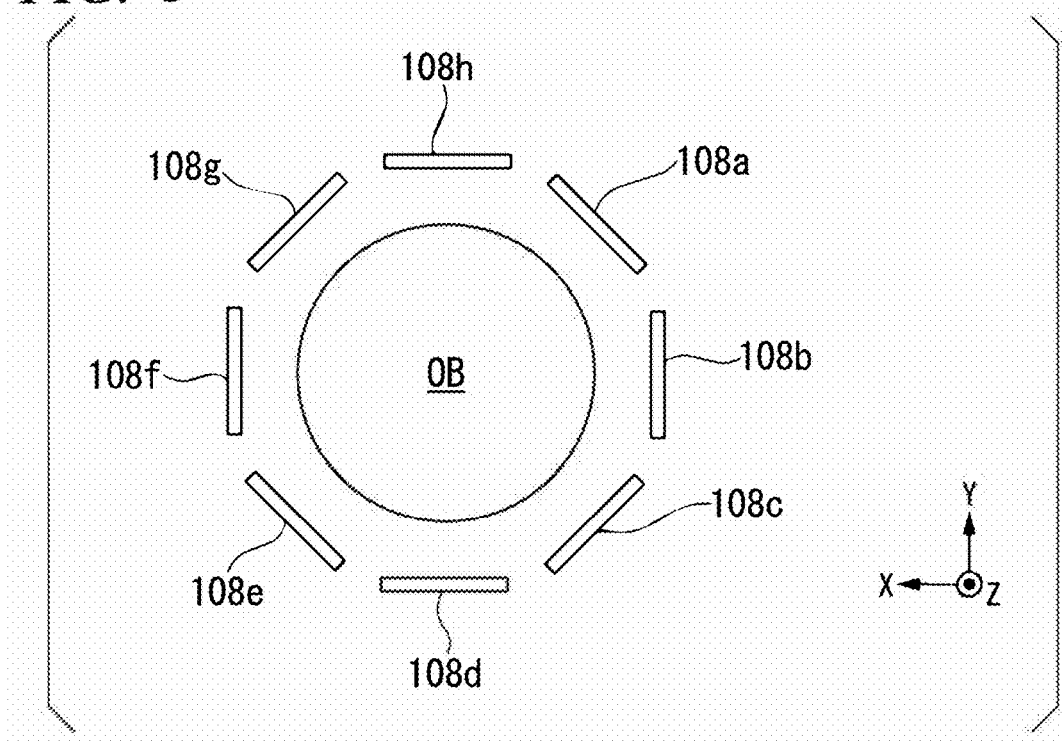
FIG. 3 is a diagram showing an example of the arrangement of a reception coil included in the MRI apparatus according to the first embodiment.

FIG. 3 is a diagram showing an example of arrangement of the reception coil 108 included in the MRI apparatus 100 according to the first embodiment. FIG. 3 shows an example in which the reception coil 108 includes eight coil elements 108a to 108h. These coil elements 108a to 108h are arranged to surround the examination object OB placed on the top board 104a. Each of the coil elements 108a to 108h receives a magnetic resonance signal generated from the examination object OB and outputs the magnetic resonance signal to the reception circuit 109.

The reception circuit 109 generates magnetic resonance data on the basis of magnetic resonance signals output from the reception coil 108 (respective coil elements). Specifically, the reception circuit 109 analog-to-digital converts magnetic resonance signals which are analog signals output from the reception coils 108 into digital signals to generate magnetic resonance data which is a digital signal. The reception circuit 109 transmits the generated magnetic resonance data to the sequence control circuit 110. Meanwhile, the reception circuit 109 may be provided in a frame apparatus including the static magnetic field magnet 101, the gradient magnetic field coil 102 and the like. When the reception coil 108 is a phased array coil, magnetic resonance signals output from the respective coil elements are appropriately distributed and combined and then output to the reception circuit 109.

The sequence control circuit 110 images the examination object OB by driving the gradient magnetic field power supply 103, the transmission circuit 107 and the reception circuit 109 on the basis of sequence information output from the console device 120. The sequence information defines a procedure for performing imaging processing. The sequence information includes information in which a level of a current supplied by the gradient magnetic field power supply 103 to the gradient magnetic field coil 102 and a timing at which the current is supplied, amplitudes and phases of RF pulses caused by the transmission circuit 107 to be generated by the transmission coil 106, a timing at which the reception circuit 109 detects a magnetic resonance signal, and the like are defined.

Meanwhile, when the sequence control circuit 110 drives the gradient magnetic field power supply 103, the transmission circuit 107 and the reception circuit 109 to image the examination object OB and receive magnetic resonance data from the reception circuit 109, the sequence control circuit 110 forwards the received magnetic resonance data to the console device 120.

The console device 120 controls the entire MRI apparatus 100 and performs magnetic resonance data reconstruction processing. For example, the console device 120 may include a communication interface 122, an input interface 124, a display 126, a processing circuit 130 and a memory (storage) 150.

The communication interface 122 includes, for example, a communication interface such as a network interface card (NIC). The communication interface 122 communicates with the medical image processing apparatus 200 through the network NW and receives information from the medical image processing apparatus 200. The communication interface 122 outputs received information to the processing circuit 130. In addition, the communication interface 122 may transmit information to other devices connected through the network NW under the control of the processing circuit 130.

The input interface 124 is an interface which receives various input operations from an operator. When the input interface 124 receives an input operation, it converts the received input operation into an electrical signal and outputs the electrical signal to the processing circuit 130. For example, the input interface 124 may be realized by a mouse, a keyboard, a trackball, a switch, a button, a joystick, a touch panel or the like. In addition, the input interface 124 may be realized by, for example, a user interface which receives audio input such as a microphone. When the input interface 124 is a touch panel, the display 126 which will be described later may be integrated with the input interface 124.

The display 126 displays various types of information. For example, the display 126 may display an image generated by the processing circuit 130 or a graphical user interface (GUI) for receiving various input operations from an operator, and the like. For example, the display 126 may be a liquid crystal display (LCD), a cathode ray tube (CRT) display, an organic electroluminescence (EL) display, or the like.

The processing circuit 130 executes, for example, an acquisition function 132, a generation function 134, a communication control function 136, and a display control function 138. For example, the processing circuit 130 may realize these functions by a hardware processor included in a computer executing a program stored in the memory 150 that is a storage device (storage circuit).

For example, a hardware processor which realizes each function of the processing circuit 130 may be circuitry such as a central processing unit (CPU), a graphics processing unit (GPU), an application specific integrated circuit (ASIC) or a programmable logic device. The programmable logic device may be a simple programmable logic device (SPLD), a complex programmable logic device (CPLD), a field programmable gate array (FPGA), or the like, for example. A program may be directly incorporated in the circuit of the hardware processor instead of being stored in the memory 150. In this case, the hardware processor realizes the aforementioned functions by reading and executing the program incorporated in the circuit thereof. The hardware processor is not limited to a hardware processor configured as a single circuit and may be configured as a single hardware processor obtained by combining a plurality of independent circuits to realize each function. In addition, a plurality of components may be integrated into a single hardware processor to realize each function.

The memory 150 is realized by a semiconductor memory element such as a random access memory (RAM) or a flash memory, a hard disk, an optical disc, or the like. These non-transitory storage media may be realized by other storage devices connected through the network NW, such as a network attached storage (NAS) and an external storage server device. Further, the memory 150 may include a non-transitory storage medium such as a read only memory (ROM) or a register.

The acquisition function 132 acquires magnetic resonance data from the sequence control circuit 110. The magnetic resonance data is obtained by analog-to-digital converting electromagnetic wave signals (magnetic resonance signals) generated from the examination object OB according to nuclear magnetic resonance, as described above. Meanwhile, data arranged in accordance with a phase encoding quantity and a frequency encoding quantity provided by the aforementioned gradient magnetic fields is also referred to as k-space data. A k-space represents a frequency space in which one-dimensional waveforms are collected when magnetic resonance signals are repeatedly collected by the reception coil 108 as the one-dimensional waveforms.

The generation function 134 performs reconstruction processing including processing such as a Fourier transform (e.g., an inverse Fourier transform) on k-space data acquired by the acquisition function 132 to generate an MR image reconstructed from the k-space data. An MR image is an example of "data generated on the basis of a reception result of an RF coil."

When the generation function 134 generates an MR image according to reconstruction, the communication control function 136 transmits the reconstructed MR image to the medical image processing apparatus 200 through the communication interface 122. In addition, the communication control function 136 may receive various types of information from the medical image processing apparatus 200 through the communication interface 122.

The display control function 138 causes the display 126 to display an MR image generated by the generation function 134. Further, when the communication interface 122 has received a medical image such as an MR image from the medical image processing apparatus 200, the display control function 138 may cause the display 126 to display the medical image received by the communication interface 122.

Example of Configuration of Medical Image Processing Apparatus

Figure 4:
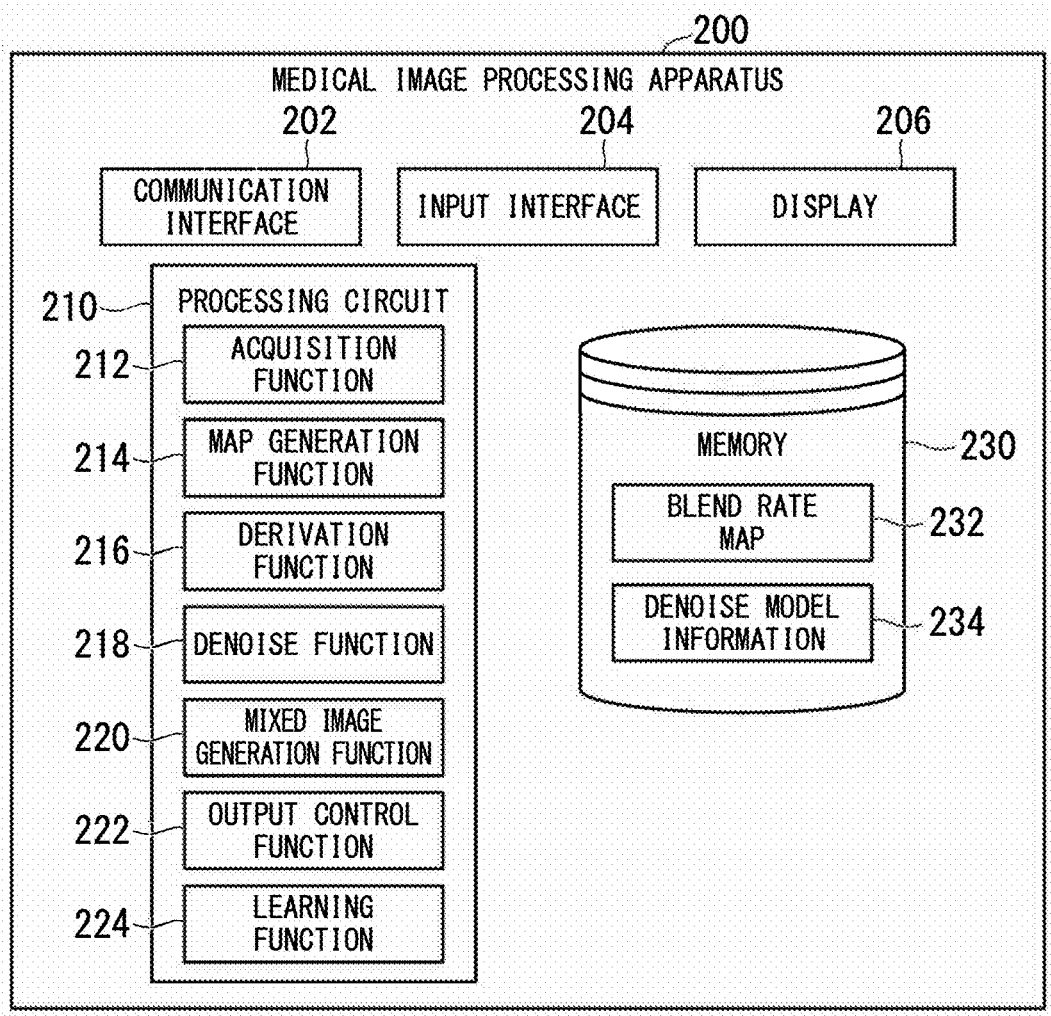
FIG. 4 is a diagram showing an example of a medical image processing apparatus according to the first embodiment.

FIG. 4 is a diagram showing an example of the medical image processing apparatus 200 according to the first embodiment. As shown in FIG. 4, the medical image processing apparatus 200 may include, for example, a communication interface 202, an input interface 204, a display 206, a processing circuit 210, and a memory 230.

The communication interface 202 includes, for example, a communication interface such as an NIC. For example, the communication interface 202 communicates with the MRI apparatus 100 through the network NW and receives a reconstructed medical image from the MRI apparatus 100. The communication interface 202 outputs the received medical image to the processing circuit 210. In addition, the communication interface 202 may transmit information to the MRI apparatus 100 or other devices connected through the network NW under the control of the processing circuit 210. The other devices may be, for example, terminal devices which can be used by image readers such as doctors and nurses.

The input interface 204 receives various input operations from an operator, converts the received input operations into electrical signals and outputs the electrical signals to the processing circuit 210. For example, the input interface 204 may be realized by a mouse, a keyboard, a track ball, a switch, a button, a joystick, a touch panel, or the like. In addition, the input interface 204 may be realized by a user interface that receives audio input such as a microphone, for example. When the input interface 204 is a touch panel, the display 206 which will be described later may be integrated with the input interface 204.

The display 206 displays various types of information. For example, the display 206 displays an image (a denoise image or a mixed image which will be described later) generated by the processing circuit 210, a GUI for receiving various input operations from an operator, and the like. For example, the display 206 may be an LCD, a CRT display, an organic EL display, or the like.

The processing circuit 210 may execute an acquisition function 212, a map generation function 214, a derivation function 216, a denoise function 218, a mixed image generation function 220, an output control function 222, and a learning function 224, for example.

A hardware processor which realizes each function of the processing circuit 210 may be circuitry such as a CPU, a GPU, an application-specific integrated circuit or a programmable logic device. A program may be directly incorporated in the circuit of the hardware processor instead of being stored in the memory 230. In this case, the hardware processor realizes the aforementioned functions by reading and executing the program incorporated in the circuit thereof. The hardware processor is not limited to a hardware processor configured as a single circuit and may be configured as a single hardware processor obtained by combining a plurality of independent circuits to realize each function. In addition, a plurality of components may be integrated into a single hardware processor to realize each function.

The memory 230 may be realized by a semiconductor memory element such as a RAM or a flash memory, a hard disk, an optical disc, or the like. These non-transitory storage media may be realized by other storage devices connected through the network NW, such as an NAS and an external storage server device. Further, the memory 230 may include a non-transitory storage medium such as a ROM or a register. For example, a blend rate map 232, denoise model information 234, and the like may be stored in the memory 230.

The blend rate map 232 is a map in which different mixing rates a are distributed in a certain space. The mixing rates a will be described later.

The denoise model information 234 is information (a program or a data structure) in which a denoise model MDL which will be described later is defined. The denoise model MDL includes, for example, one or more deep neural networks (DNNs).

For example, the denoise model information 234 may include combination information representing how neurons (units or nodes) included in an input layer, one or more hidden layers (middle layers) and an output layer constituting each DNN included in the denoise model MDL are combined, weight information representing the number of combination coefficients assigned to data input and output between combined neurons, and the like. For example, the combination information may include information designating the number of neurons included in each layer or the type of a neuron that is a combination destination of each neuron, and information on an activation function that realizes each neuron, and gates provided between neurons of the hidden layers, or the like. The activation function that realizes a neuron may be a function (a rectified linear unit (ReLU) function, an exponential linear unit (ELU) function or a clipping function) that switches between operations in response to input code, a Sigmoid function, a step function, a hyperbolic tangent function, or an identity function, for example. A gate selectively passes or weights data transferred between neurons in response to a value (e.g., 1 or 0) returned according to the activation function, for example. The combination coefficient includes a weight assigned to output data when the data is output from a neuron of a certain layer to a neuron of a deeper layer in a hidden layer of a neural network, for example. Further, the combination coefficient may include a unique bias component of each layer, and the like.

The acquisition function 212 acquires a medical image from the MRI apparatus 100 through the communication interface 202. The acquisition function 212 causes the memory 230 to store the acquired medical image.

The map generation function 214 generates a coil sensitivity map SM from medical images acquired by the acquisition function 212. The coil sensitivity map SM is an example of "information about reception characteristics of an RF coil" and a "reception sensitivity map."

The coil sensitivity map SM represents spatial sensitivity distributions of magnetic resonance signals received through respective coil elements included in a phased array coil of the MRI apparatus 100. For example, the map generation function 214 may generate the coil sensitivity map SM on the basis of medical images (hereinafter referred to as reference images) acquired through pre-scanning.

Pre-scanning is scanning performed prior to main scanning and involves scanning the examination object OB at least once in order to perform calibration such as coil tuning, setting of a center frequency, and reception sensitivity adjustment, for example. Main scanning involves scanning the examination object OB on the basis of sequence information also called a pulse sequence, for example. Meanwhile, the coil sensitivity map SM need not be obtained through pre-scanning and may be acquired after main scanning.

In addition, pre-scanning may be a part of a plurality of scanning operations sequentially performed as main scanning. Pre-scanning may be performed before the bed 104 (top board 104a) on which the examination object OB is placed is inserted into the hollow of the gradient magnetic field coil 102 or when the examination object OB is not placed on the bed 104.

For example, the map generation function 214 may generate a sensitivity map SM of each coil element by dividing a first reference image by a second reference image. The first reference image is an image acquired when each coil element of the phased array coil is caused to receive magnetic resonance signals generated from the examination object OB when the whole body coil is caused to transmit RF pulses. The second reference image is an image acquired when the whole body coil is caused to receive magnetic resonance signals generated from the examination object OB when the whole body coil is caused to transmit RF pulses. "Dividing by an image" is to divide pixel values by pixels at the same positions from among a plurality of pixels included in the first reference image and the second reference image, for example.

In addition, the map generation function 214 may generate the coil sensitivity map SM of the phased array coil by obtaining the sums of squares of first reference images corresponding to respective coil elements and dividing a medical image having the sums of squares as pixel values by the second reference image.

Figure 5:
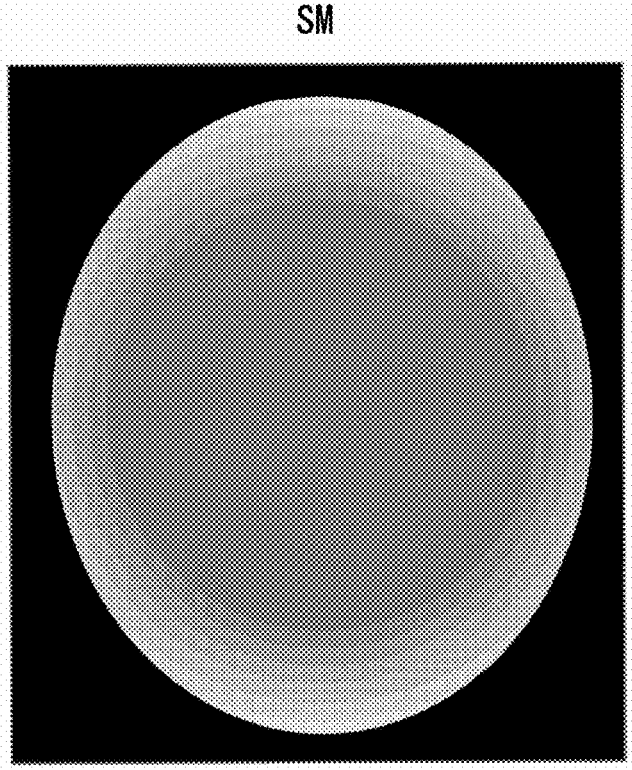
FIG. 5 is a diagram showing an example of a coil sensitivity map according to the first embodiment.

FIG. 5 is a diagram showing an example of the coil sensitivity map SM according to the first embodiment. The coil sensitivity map SM shown in the figure represents higher sensitivity as the color is closer to white.

In addition, the map generation function 214 may generate a geometric-factor (g-factor) map GM instead of or in addition to the coil sensitivity map SM generated from a reference image acquired by the acquisition function 212. The g-factor map GM is another example of the "information about reception characteristics of an RF coil."

The g-factor map GM represents a spatial distribution of g-factors that contribute to expansion performance in parallel imaging. The parallel imaging is a method of reducing a scan time using coil sensitivity differences in respective coil elements included in a phased array coil. In the parallel imaging, a magnetic resonance signal emitted from the examination object OB is received by the respective coil elements simultaneously (in parallel). A g-factor is an index value indicating easiness of separation when folding of images (overlapping of images) is separated (expanded) in image reconstruction processing. The g-factor is an index value depending on, for example, relative positions of coil elements in a phased array coil, phase directions of the coil elements, and the like. A smaller g-factor indicates easier separation and higher independency between coil elements. In addition, a larger g-factor indicates more difficult separation and lower independency between coil elements.

Figure 6:
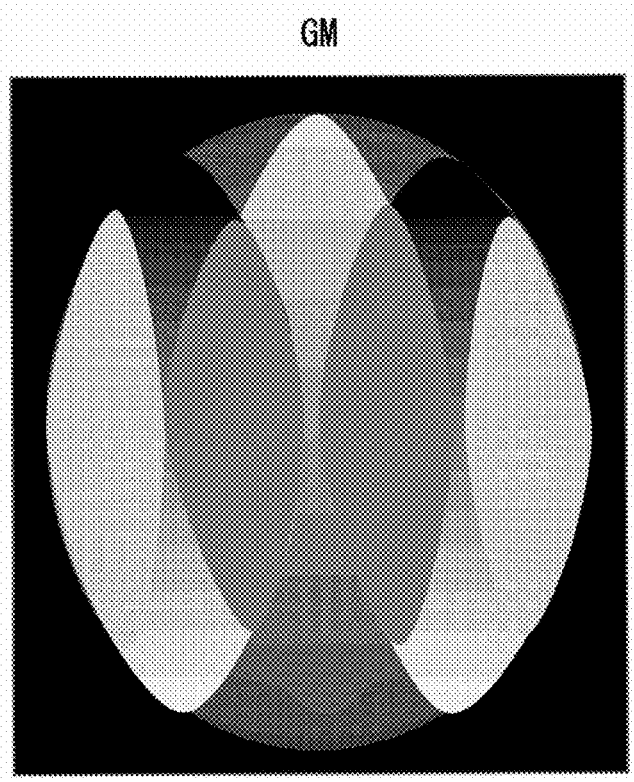
FIG. 6 is a diagram showing an example of a g-factor map according to the first embodiment.

FIG. 6 is a diagram showing an example of the g-factor map GM according to the first embodiment. The g-factor map GM as shown in the figure may vary according to disposition of coil elements, a double-speed rate (thinning rate) in parallel imaging, a phase encoding direction, and the like.

When at least one of the coil sensitivity map SM and the g-factor map GM is generated, the map generation function 214 generates a blend rate map 232 on the basis of the generated map. For example, the map generation function 214 may generate a blend rate map 232 in which a mixing rate a is low at a position where coil sensitivity is high and high at a position where coil sensitivity is low when the coil sensitivity map SM is generated. That is, the map generation function 214 generates a blend rate map 232 that is inverse to the coil sensitivity map SM. In addition, the map generation function 214 may generate a blend rate map 232 in which a mixing rate a is high at a position where a g-factor is high and low at a position where the g-factor is low when the g-factor map GM is generated. That is, the map generation function 214 may generate a blend rate map 232 in which mixing rates a are distributed with the same tendency as distribution of g-factors in the g-factor map GM. When the map generation function 214 generates a blend rate map 232, the map generation function 214 stores the blend rate map 232 in the memory 230. The blend rate map 232 is an example of a "third map."

The derivation function 216 derives, on the basis of a medical image (hereinafter referred to as an original image) acquired by the acquisition function 212, an index value with respect to noise included in the original image. For example, the derivation function 216 derives an SNR as the index value with respect to the noise. An SNR is an index value obtained by dividing a signal intensity of an image by a signal intensity of noise. An SNR derivation method will be described later in detail.

The denoise function 218 removes noise from an original image acquired by the acquisition function 212 using a denoise model MDL represented by the denoise model information 234. The denoise model MDL may be realized as a part of the denoise function 218, for example, by a processor executing the denoise model MDL.

For example, the denoise model MDL may be realized by a convolutional neural network (CNN) and the CNN may have a configuration in which a convolutional layer, an activation layer and the like are arranged in multiple layers.

Figure 7:
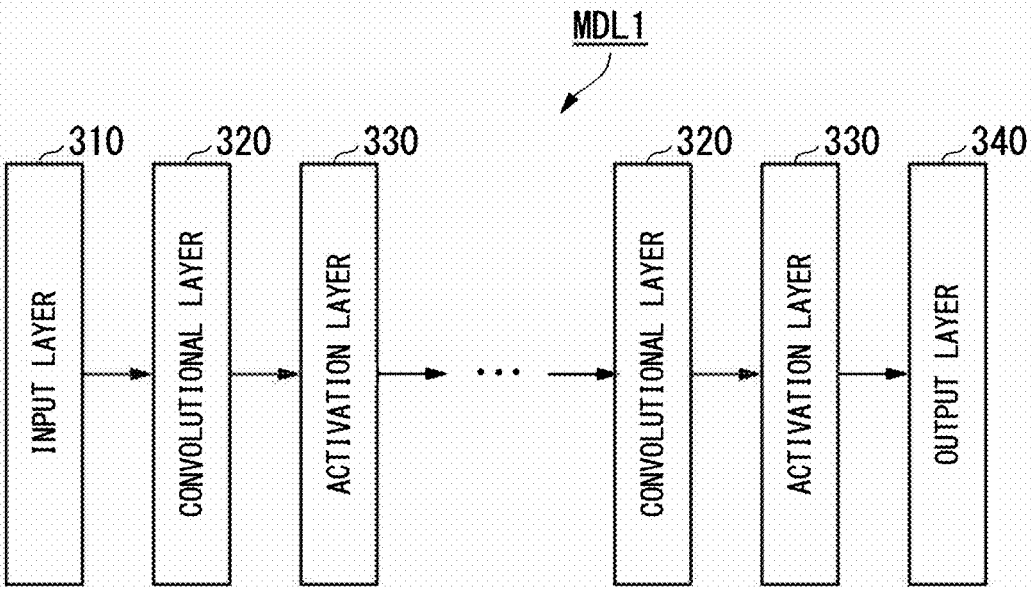
FIG. 7 is a diagram showing an example of a configuration of a denoise model according to the first embodiment.

FIG. 7 is a diagram showing an example of a configuration of the denoise model MDL according to the first embodiment. As shown, the denoise model MDL may include, for example, an input layer 310, one or more convolutional layers 320, one or more activation layers 330, and an output layer 340.

For example, when an original image is regarded as a matrix having elements corresponding to respective pixels, the matrix corresponding to the original image is input to the input layer 310. The input layer 310 performs application of a bias component to the input matrix at a suitable time, or the like and outputs the input matrix to which the bias component has been applied to the convolutional layer 320 at the following stage.

The convolutional layer 320 repeats a product-sum operation on the input matrix while sliding a linear transformation matrix called a filter or a kernel by a certain determined slide amount to generate a matrix including a plurality of elements with which product sums with the linear transformation matrix are associated as element values from the input matrix. Here, the convolutional layer 320 may perform padding (e.g., zero padding) in which an element having any value around the input matrix is interpolated to convert the matrix input to the convolutional layer 320 to a matrix having the same numbers of rows and columns as the matrix of the original image input to the input layer 310. Then, the convolutional layer 320 outputs the generated matrix to the activation layer 330.

The activation layer 330 performs calculation of an activation function on each element of the matrix input from the convolutional layer 320 and outputs the matrix on which the calculation has been performed to the layer at the following stage.

Figure 8:
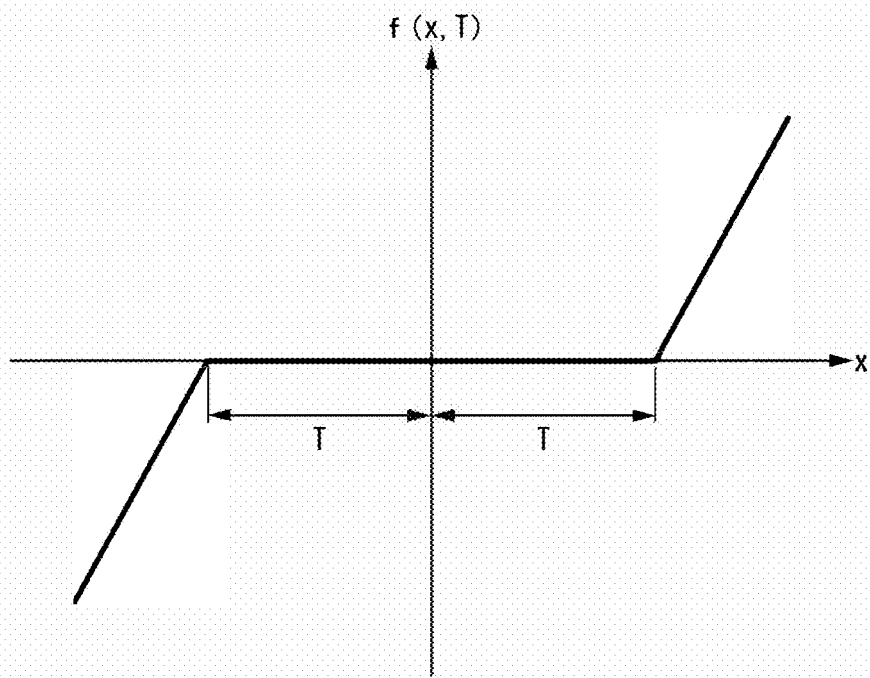
FIG. 8 is a diagram representing an example of an activation function of an activation layer according to the first embodiment.

FIG. 8 is a diagram representing an example of the activation function of the activation layer 330 according to the first embodiment. As in the example provided, the activation function of the activation layer 330 may be a Soft-Shrinkage function. The Soft-Shrinkage function is represented by mathematical expression (1) below, for example. Further, the activation function of the activation layer 330 may be a Hard-Shrinkage function instead of the Soft-Shrinkage function.

[Expression. 1]

$$f(x, T) = \begin{cases} x - T & (x > T) \\ x + T & (x < -T), T \geq 0 \\ 0 & \text{otherwise} \end{cases} \quad (1)$$

The Soft-Shrinkage function or the Hard-Shrinkage function outputs 0 when an element value x that is an input value is within a range of a predetermined positive and negative threshold values ±T having 0 as the center and outputs a value proportional to the element value x when the element value x that is an input value exceeds the positive threshold value +T or is less than the negative threshold value −T. It is possible to make an image signal having an amplitude less than the threshold value T, that is, a weak image signal that is highly likely to be noise to be zero at the output of the activation function, by applying the Soft-Shrinkage function or the Hard-Shrinkage function to the activation function of the activation layer 330. The negative threshold value −T is an example of a "first threshold value" and the positive threshold value +T is an example of a "second threshold value."

The threshold value T is a parameter varying according to a noise level (signal intensity or signal power) included in an input image and is represented by mathematical expression (2) below, for example.

[Expression. 2]

$$T = \beta \times G \quad (2)$$

G in mathematical expression (2) represents an internal parameter depending on a noise level included in an input image. The denoise function 218 determines the internal parameter G according to an SNR of an input image derived by the derivation function 216. For example, the denoise function 218 may decrease the internal parameter G as the SNR of the input image increases, that is, the input image has higher definition and increase the internal parameter G as the SNR of the input image decreases, that is, the input image has lower definition.

β in mathematical expression (2) is a weighting factor multiplied by a noise level. The weighting factor is determined by machine learning. As represented by mathematical expression (2), it is possible to make the activation function of the activation layer 330 to be an activation function reacting on signals equal to or greater than a specific strength by varying the threshold value T. As a result, it is possible to remove noise from an original image with high accuracy even if a signal intensity of noise included in the original image varies.

The output layer 340 outputs the matrix processed by the convolutional layer 320 and the activation layer 330 at the previous stage. The denoise function 218 acquires the matrix output by the output layer 340 of the denoise model MDL as a medical image (hereinafter referred to as a denoise image) obtained by removing noise from the original image.

Meanwhile, the denoise model MDL exemplified in FIG. 7 is merely an example and, for example, a pooling layer or the like may be included. The pooling layer compresses (reduces) the number of dimensions of an input matrix by replacing element values of the input matrix with a representative value such as an average value or a maximum value of all of the element values included in the matrix. The pooling layer outputs the matrix having a compressed number of dimensions to the layer at the following stage.

The mixed image generation function 220 generates a mixed image (composite image) by mixing (compositing) the original image acquired by the acquisition function 212 and the denoise image from which noise has been removed by the denoise function 218. This processing is image compositing processing also called alpha blending.

Figure 9:
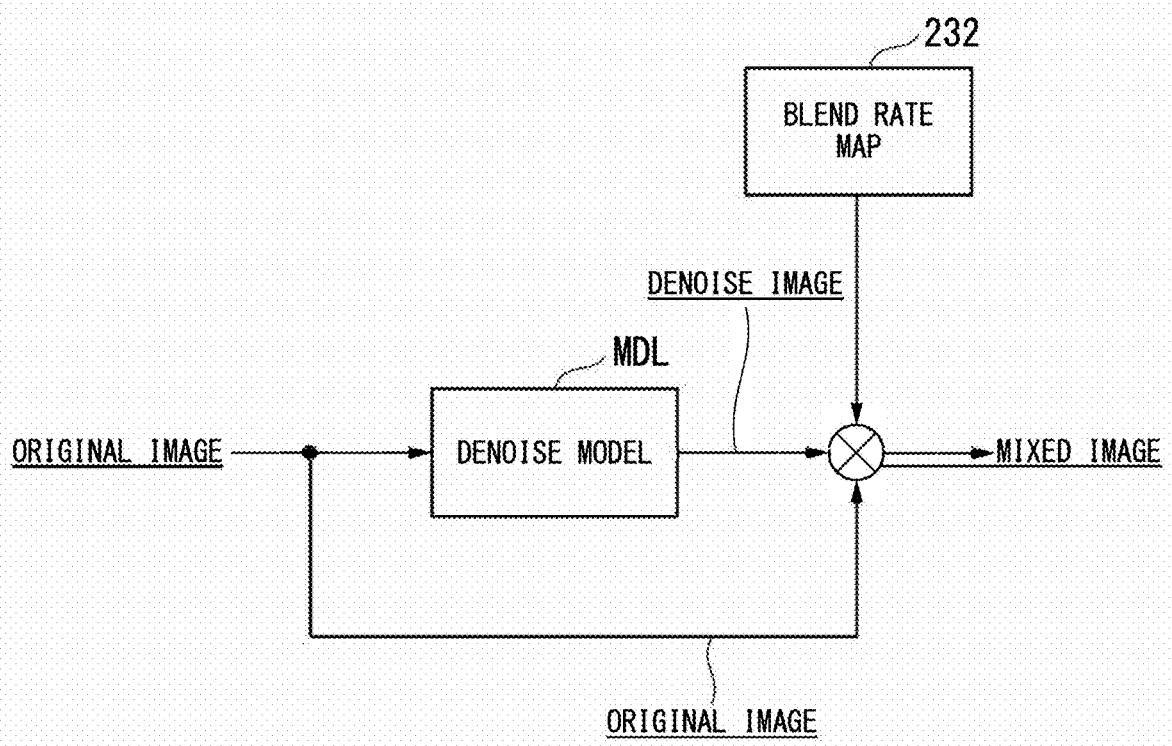
FIG. 9 is a diagram showing an example of a configuration of generating a mixed image.

FIG. 9 is a diagram showing an example of a configuration of generating a mixed image. As in an shown example, the mixed image generation function 220 generates a mixed image by mixing an original image input to the denoise model MDL and a denoise image output from the denoise model MDL on the basis of a blend rate map 232. Mixing (compositing) is to add element values of elements $e_{ij}$ in the same rows i and columns j among a plurality of elements included in an original image and a denoise image and to use the sums of added element values as element values of elements $e_{ij}$ in a mixed image. The mixed image generation function 220 multiplies each element by a mixing rate a as a weighting factor when element values are added. A mixed image generation expression may be represented by mathematical expression (3), for example.

[Expression. 3]

$$IMG_{MIX} = \alpha(x) \times IMG_{original} + (1 - \alpha(x)) \times IMG_{denoise} \quad (3)$$

$IMG_{MIX}$ in mathematical expression (3) represents a mixed image, $IMG_{original}$ represents an original image, and $IMG_{denoise}$ represents a denoise image. In addition, x represents coil sensitivity or a g-factor, $\alpha(x)$ represents a mixing rate using the coil sensitivity or a g-factor as a variable. For example, the mixed image generation function 220 may multiply element values of the original image by the coefficient $\alpha(x)$, multiply element values of the denoise image by a coefficient $(1-\alpha(x))$ and use the sums of the resultant values as element values of the mixed image.

When the mixed image generation function 220 generates the mixed image, the output control function 222 transmits the mixed image to the MRI apparatus 100 through the communication interface 202. In addition, the output control function 222 may cause the display 206 to display the mixed image.

The learning function 224 inputs an original image regarded as certain teacher data to the denoise model MDL and learns the denoise model MLD such that a denoise image output from the denoise model MDL approaches an image associated with the original image regarded as the teacher data in advance as a teacher label. For example, the image regarded as the teacher label may be an image having an SNR that has increased by increasing a sampling frequency or the like, and the original image input to the denoise model MDL as the teacher data may be an image obtained by applying known noise to the image having an SNR that has increased by increasing a sampling frequency or the like. The known noise may be Gaussian noise, for example.

For example, the learning function 224 learns various parameters such as element values of a linear transformation matrix of the convolutional layer 320 and the weighting factor $\beta$ of the activation function of each node of the activation layer 330 using a stochastic gradient descent method such as stochastic gradient descent (SGD), momentum SGD, AdaGrad, RMSprop, AdaDelta or adaptive moment estimation (Adam) such that differences between denoise images output from the denoise model MDL and teacher data images decrease.

[Processing Flow]

Figure 10:
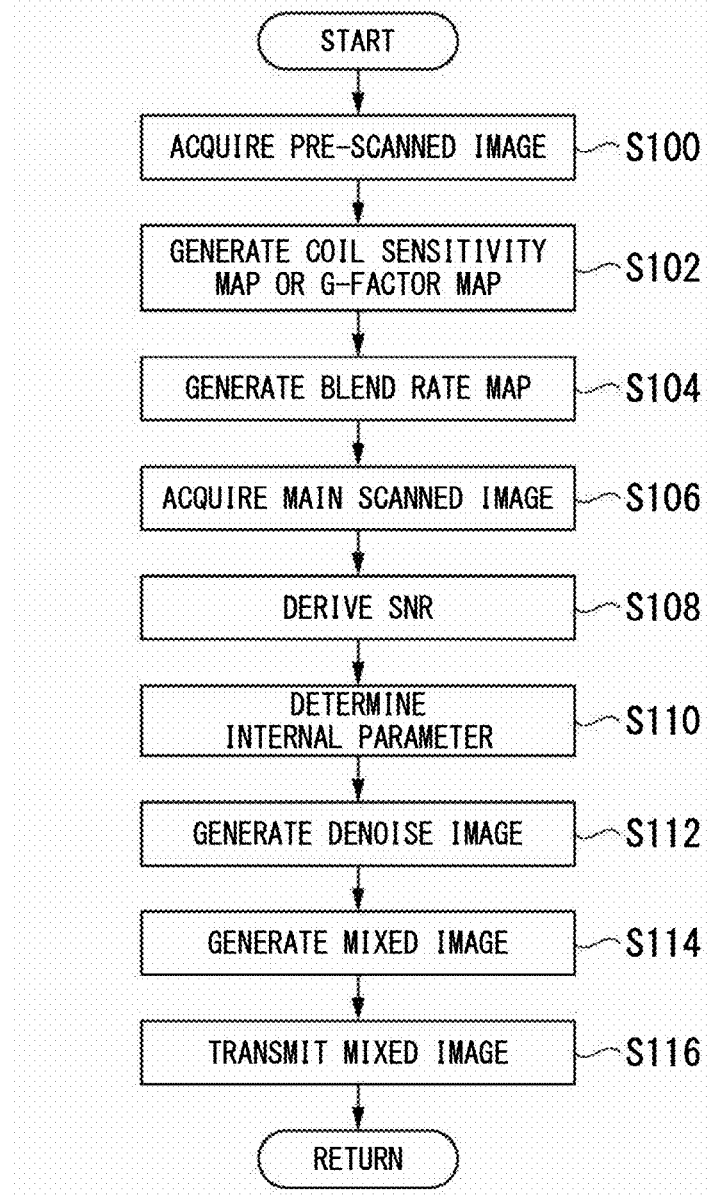
FIG. 10 is a flowchart showing a processing flow of a processing circuit according to the first embodiment.

Hereinafter, a processing flow of the processing circuit 210 according to the first embodiment will be described on the basis of a flowchart. FIG. 10 is a flowchart showing a processing flow of the processing circuit 210 according to the first embodiment. Processing of this flowchart may be repeatedly performed at a predetermined interval, for example.

The acquisition function 212 acquires a medical image obtained using pre-scanning, that is, a reference image, from the MRI apparatus 100 through the communication interface 202 (step S100).

Next, the map generation function 214 generates a coil sensitivity map SM or a g-factor map GM from the reference image acquired by the acquisition function 212 (step S102) and generates a blend rate map 232 on the basis of at least one map (step S104).

Next, the acquisition function 212 acquires a medical image obtained using main scanning (hereinafter referred to as a main scanned image) from the MRI apparatus 100 through the communication interface 202 (step S106).

Next, the derivation function 216 derives an SNR of the main scanned image acquired by the acquisition function 212 (step S108).

For example, the derivation function 216 derives the SNR of the main scanned image on the basis of imaging conditions during main scanning. The imaging conditions may include parameters such as the number of matrices, a receiver gain, the number of times of imaging addition, and a reception bandwidth, for example. The number of matrices is a parameter indicating the number of pixels of a medical image in order to determine a resolution of the medical image (resolution of the MRI apparatus 100). The receiver gain is a parameter indicating a gain of a reception system such as the reception coil 108 and the reception circuit 109. The number of times of imaging addition is a parameter indicating the number of times of repeated scanning for the same slice. The reception bandwidth is a parameter indicating a sampling frequency when a magnetic resonance signal emitted from the examination object OB is read. These parameters are treated as hyper parameters because they need to be set, for example, by a user such as a doctor or an engineer during scanning. Meanwhile, the imaging conditions may include parameters such as a slice thickness, an imaging visual field, a flip angle, and a phase encoding direction in addition to or instead of the aforementioned parameters.

Noise that may be included in a medical image includes Gaussian noise caused by thermal noise of a reception system. It is known that thermal noise varies according to imaging conditions. Accordingly, the derivation function 216 derives the SNR of the main scanned image by inputting parameters included in the imaging conditions during main scanning to a function derived using some or all of the plurality of parameters such as the number of matrices, the receiver gain, the number of times of imaging addition, and the reception bandwidth as explanatory variables and using the SNR as an objective variable.

In addition, when a plurality of main scanned images are acquired by the acquisition function 212, the derivation function 216 may derive SNRs of the main scanned images on the basis of differences between pixel values of an image with RF pulses and an image without RF pulses from among the plurality of main scanned images. The image with RF pulses is a main scanned image obtained when RF pulses have been transmitted from the transmission coil 106 in a state in which the gradient magnetic field coil 10 has generated gradient magnetic fields. The image without RF pulses is a main scanned image obtained when no RF pulse has been transmitted from the transmission coil 106 in a state in which the gradient magnetic field coil 10 has generated gradient magnetic fields.

Furthermore, when a plurality of main scanned images are acquired by the acquisition function 212, the derivation function 216 may derive SNRs of the main scanned images on the basis of differences between pixel values of two or more images with RF pulses acquired when RF pulses have been transmitted to the same examination object $OB_A$ from among the plurality of main scanned images. In this case, the derivation function 216 may derive the SNRs of the main scanned images on the basis of differences between pixel values of two or more images with RF pulses close to a center slice. For example, when main scanning is a sequence in which scanning is repeated 10 times, the center slice is an image acquired by the fifth or sixth scanning.

In this manner, magnetic resonance signal components can be cancelled each other and an SNR can be obtained on the basis of a random noise component caused by thermal noise of the reception system by obtaining a difference between two original images acquired by performing scanning multiple times under the condition of the same examination object OB.

Next, the denoise function 218 determines an internal parameter G according to the SNR of the main scanned image derived by the derivation function 216 (step S110).

Next, the denoise function 218 generates a denoise image by removing noise from the main scanned image acquired by the acquisition function 212 using a denoise model MDL having the determined internal parameter G (step S112).

Next, the mixed image generation function 220 generates a mixed image by mixing the main scanned image from which the SNR has been obtained and the denoise image obtained by removing noise from the main scanned image on the basis of the blend rate map 232 (step S114).

For example, even when noise has been removed from an original image using a sufficiently trained denoise model MDL, a desired structure such as a tumor or an organ is likely to be removed as noise due to the influence of a ununiform distribution of noise according to an RF coil sensitivity distribution or a g-factor distribution. Accordingly, it is possible to improve the accuracy of diagnosis by increasing a mixing degree of an original image from which a structure has not been removed according to noise strength.

Next, the output control function 222 controls the communication interface 202 to transmit the mixed image generated by the mixed image generation function 220 to the MRI apparatus 100 or the like (step S116). The display control function 138 of the MRI apparatus 100 receives the mixed image and causes the display 126 to display the mixed image. Accordingly, processing of this flowchart ends.

According to the above-described first embodiment, the processing circuit 210 acquires a medical image generated on the basis of a reception result of the reception coil 108 which has received a magnetic resonance signal and performs denoise on the medical image. The processing circuit 210 determines mixing rates of the medical image before the denoise is performed and the medical image on which the denoise has been performed on the basis of at least one of a coil sensitivity map SM and a g-factor map GM which are reception characteristics of the reception coil 108. Then, the processing circuit 210 generates a mixed image by mixing the medical image before the denoise is performed and the medical image on which the denoise has been performed according to the determined mixing rates. Accordingly, it is possible to generate a medical image which can further improve diagnosis accuracy.

For example, even when a desired structure such as a lesion has been removed from an original image according to denoise, the desired structure remains in a mixed image in which the original image is included in a proportion of a mixing rate a and thus diagnosis accuracy can be improved.

In addition, according to the above-described first embodiment, it is possible to prevent addition of locally amplified noise because an original image and a denoise image are mixed on the basis of the blend rate map 232 in which mixing rates a are different at respective positions in an image space. For example, in a blend rate map 232 using the coil sensitivity map SM, the mixing rate a decreases at a position where coil sensitivity is high and increases at a position where coil sensitivity is low. Accordingly, it is possible to increase the proportion of an original image with respect to a region of an image in which coil sensitivity easily decreases when a mixed image is generated. On the other hand, it is possible to decrease the proportion of the original image with respect to a region of an image in which coil sensitivity easily increases. As a result, it is possible to generate a medical image in which a desired structure remains while reducing noise as compared to a case in which all pixels of an original image are multiplied by a uniform mixing rate a on the premise that a noise distribution is spatially uniform.

Furthermore, according to the above-described first embodiment, it is possible to urge a user to change imaging conditions such that medical images with higher definition can be obtained and perform re-scanning because a mixed image can be provided to the user through the MRI apparatus 100. For example, when an SNR of an original image is low irrespective of a coil sensitivity and a g-factor and the original image has a low definition, a mixed image also has a low definition. Accordingly, it is possible to allow the user to recognize that a desired structure has not been extracted on the original image and diagnosis accuracy is highly likely to decrease. As a result, it is possible to urge the user to change imaging conditions and perform re-scanning.

Modified Example of First Embodiment

Hereinafter, a modified example of the first embodiment will be described. Although the MRI apparatus 100 and the medical image processing apparatus 200 are different apparatuses in the above-described first embodiment, the present invention is not limited thereto. For example, the medical image processing apparatus 200 may be realized by a function of the console device 120 of the MRI apparatus 100. That is, the medical image processing apparatus 200 may be a virtual machine virtually realized by the console device 120 of the MRI apparatus 100.

Figure 11:
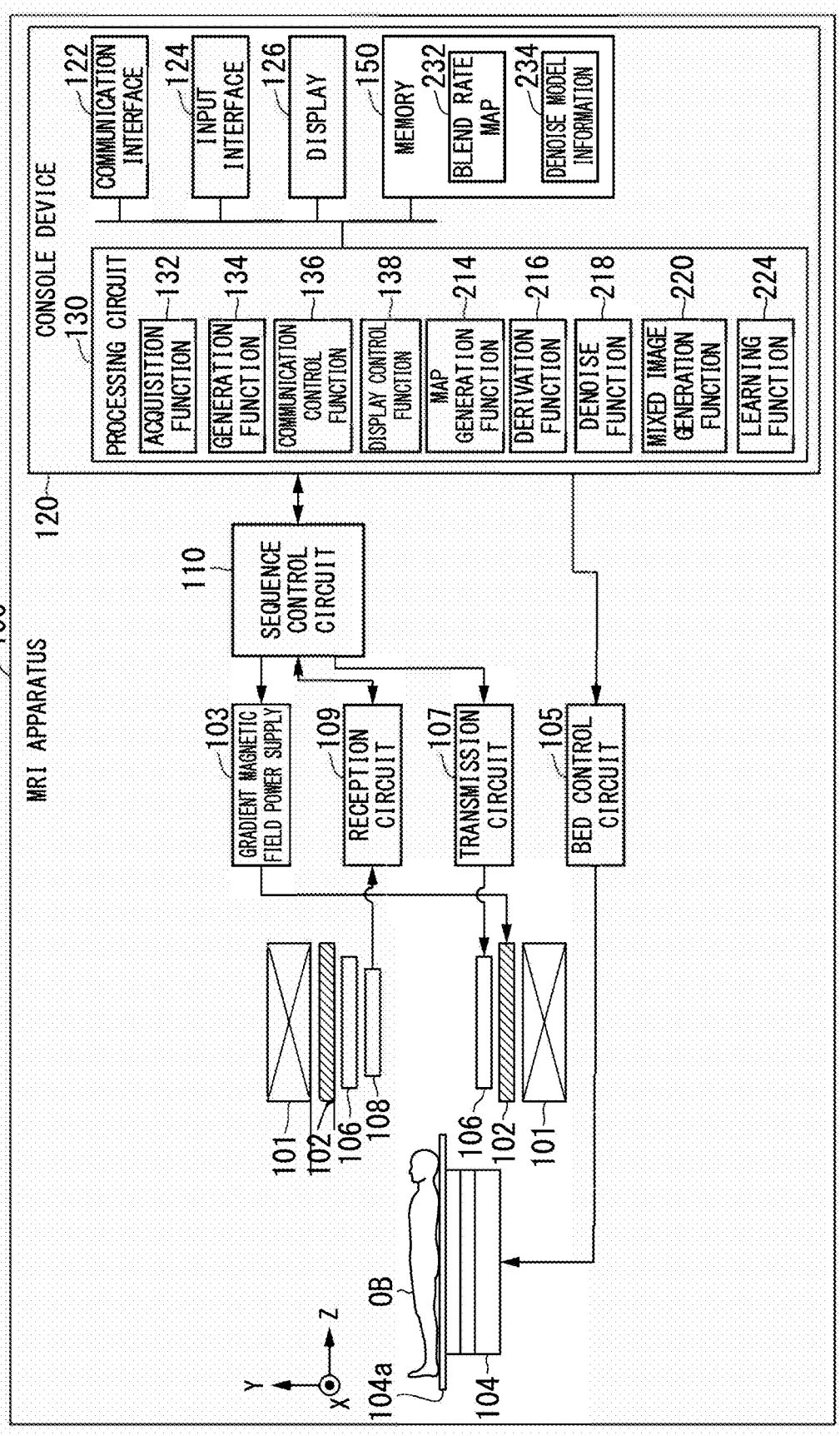
FIG. 11 is a diagram showing another example of the MRI apparatus according to the first embodiment.

FIG. 11 is a diagram showing another example of the MRI apparatus 100 according to the first embodiment. As shown in FIG. 11, the processing circuit 130 of the console device 120 may execute the acquisition function 212, the map generation function 214, the derivation function 216, the denoise function 218, the mixed image generation function 220 and the learning function 224 in addition to the above-described acquisition function 132, generation function 134, communication control function 136 and display control function 138.

In addition, the memory 150 of the console device 120 may store the blend rate map 232 and the denoise model information 234.

According to this configuration, it is possible to generate a medical image which can improve diagnosis accuracy using only the MRI apparatus 100.

In addition, although the processing circuit 210 performs denoise on a medical image (original image) acquired from the MRI apparatus 100 in the above-described first embodiment, the present invention is not limited thereto. For example, the processing circuit 210 may perform denoise on various types of data before reconstruction which are received from the MRI apparatus 100 (e.g., a magnetic resonance signal, k-space data corresponding to the magnetic resonance signal, and the like). In this case, a magnetic resonance signal and k-space data are another example of "data generated on the basis of a reception result of an RF coil."

Second Embodiment

Hereinafter, a second embodiment will be described. In the above-described first embodiment, the processing circuit 210 determines mixing rates when an original image before denoise is performed and a denoise image on which denoise has been performed are mixed on the basis of the coil sensitivity map SM and the g-factor map GM. In contrast, the second embodiment differs from the above-described first embodiment in that the processing circuit 210 determines strength of the denoise on the basis of the g-factor map GM. Hereinafter, a description will be made focusing on differences from the first embodiment and common points in the first and second embodiments will be omitted. Meanwhile, in description of the second embodiment, the same parts as those of the first embodiment are denoted by the same reference signs and described using the same.

The denoise function 218 according to the second embodiment determines the strength of the denoise on the basis of a g-factor map GM when the map generation function 214 generates the g-factor map GM. The strength of the denoise is an index indicating an image signal intensity degree to which noise is removed from an original image.

For example, the denoise function 218 determines the strength of the denoise by adjusting a threshold value T of an activation function such as a Soft-Shrinkage function or a Hard-Shrinkage function according to mathematical expression (4).

[Expression. 4]

$$T = \beta \times G \times w(p) \quad (4)$$

A parameter G is determined on the premise that noise such as thermal noise is spatially uniform. That is, the parameter G does not vary for each pixel. On the other hand, folding of images (overlapping of images) may occur in parallel imaging, and thus noise may also be duplicated in an image region where an image is folded. Accordingly, the threshold value T is varied according to pixel positions by multiplying the product of a weighting factor $\beta$ determined by machine learning and the parameter G varying according to noise levels by a weighting factor w(p) varying according to pixel positions on an image in the second embodiment. The weighting factor is an example of a "first parameter" and the parameter G is an example of a "second parameter."

The weighting factor w(p) may be the aforementioned g-factor map GM. That is, the weighting factor w(p) may be a coefficient set having g-factors as coefficients. In addition, the weighting factor w(p) may be a value obtained by multiplying a g-factor by any weighting factor or adding a bias component to a g-factor.

When the weighting factor $\beta$ is trained in advance, the weighting factor w(p) may be uniform on an image without depending on pixel positions. In other words, the weighting factor $\beta$ is trained under the condition that noise of an image is spatially uniform. In this manner, it is possible to appropriately set the threshold value T for an image region in which noise has been added according to parallel imaging by determining the weighting factor $\beta$ while making the weighting factor w(p) uniform during training and varying the weighting factor w(p) according to pixel positions on the basis of a g-factor map GM which may vary according to imaging conditions during inference. As a result, it is possible to remove ununiform noise from an image having a ununiform spatial noise distribution and uniformize a noise quantity of an original image returned to a denoise image according to mixing rates.

According to the above-described second embodiment, the processing circuit 210 acquires data generated on the basis of a signal received by an RF coil (e.g., a medical image, k-space data, and the like) and a g-factor map GM. The processing circuit 210 determines the strength of the denoise on the basis of the acquired g-factor map GM. Then, the processing circuit 210 performs the denoise on the acquired data according to the determined strength of the denoise. Accordingly, it is possible to remove ununiform noise from an image having a spatially ununiform noise distribution and uniformize a noise quantity of an original image returned to a denoise image according to mixing rates.

Meanwhile, although the strength of denoise is determined by adjusting the threshold value T of the activation function such as a Soft-Shrinkage function or a Hard-Shrinkage function on the basis of the g-factor map GM in the above-described second embodiment, the present invention is not limited thereto. For example, the technique such as determining the strength of denoise on the basis of the g-factor map GM may also be applied to other techniques such as performing denoise according to a noise quantity of an image, for example (e.g., block matching and 3D collaborative filtering (BM3D) and the like).

In addition, the processing circuit 210 may perform denoise on various types of data before reconstruction which are received from the MRI apparatus 100 as in the above-described first embodiment.

In this case, first, the acquisition function 212 acquires a medical image obtained by pre-scanning from the MRI apparatus 100 as a reference image through the communication interface 202.

Next, the map generation function 214 generates a g-factor map GM from the reference image acquired by the acquisition function 212.

Next, the acquisition function 212 acquires various types of data obtained by main scanning (e.g., a medical image, a magnetic resonance signal, k-space data, and the like) from the MRI apparatus 100 through the communication interface 202.

Next, the derivation function 216 derives an SNR of the data acquired by the acquisition function 212.

Next, the denoise function 218 determines the threshold value T of the activation function of the denoise model MDL. Specifically, the denoise function 218 determines the internal parameter G according to the SNR derived by the derivation function 216 and generates the weighting factor w(p) on the basis of the g-factor map GM generated by the map generation function 214. Accordingly, the threshold value T is determined.

Next, the denoise function 218 removes noise from the data acquired by the acquisition function 212 using the denoise model MDL in which the threshold value T of the activation function has been determined to generate a denoise image. When a denoise target is a magnetic resonance signal and k-space data, the denoise function 218 may generate a medical image through reconstruction from the magnetic resonance signal and the k-space data on which denoise has been performed.

Next, the mixed image generation function 220 may generate a mixed image by mixing a medical image based on the data before denoise is performed and a medical image based on the data after the denoise has been performed on the basis of the blend rate map 232.

For example, when a denoise target is a magnetic resonance signal and k-space data, a "medical image based on data before denoise is performed" is a medical image generated through reconstruction from the magnetic resonance signal and the k-space data on which denoise has not been performed yet. Similarly, when a denoise target is a magnetic resonance signal and k-space data, a "medical image based on data after denoise has been performed" is a medical image generated through reconstruction from the magnetic resonance signal and the k-space data on which denoise has already been performed.

On the other hand, when a denoise target is a medical image, a "medical image based on data before denoise is performed" is a medical image on which denoise has not been performed yet. Similarly, when a denoise target is a medical image, a "medical image based on data after denoise is performed" is a medical image on which denoise has already been performed. That is, a "medical image based on data" may be replaced by a "medical image."

Next, the output control function 222 controls the communication interface 202 to transmit the mixed image generated by the mixed image generation function 220 to the MRI apparatus 100 or the like. The display control function 138 of the MRI apparatus 100 receives the mixed image and causes the display 126 to display the mixed image.

Meanwhile, the output control function 222 may control the communication interface 202 to transmit a denoise image generated by the denoise function 218 to the MRI apparatus 100 or the like.

Any of the above-described embodiments can be represented as follows.

A medical image processing apparatus includes:
a storage which stores a program; and
a processor,
wherein the processor is configured, by executing the program:
to acquire a medical image generated on the basis of a reception result of an RF coil which receives an MR signal acquired by applying radio-frequency magnetic fields to an examination object;
to perform denoise on the medical image;
to generate a mixed image by mixing a first medical image before the denoise is performed and a second medical image after the denoise is performed; and
to determine mixing rates of the first medical image and the second medical image on the basis of reception characteristics of the RF coil.

According to at least one of the above-described embodiments, the processing circuit 210 acquires a medical image generated on the basis of a reception result of the reception coil 108 which has received a magnetic resonance signal and performs denoise on the medical image. The processing circuit 210 determines mixing rates of a medical image before the denoise is performed and a denoise image on which the denoise has been performed on the basis of at least one of a coil sensitivity map SM and a g-factor map GM which are reception characteristics of the reception coil 108. Then, the processing circuit 210 generates a mixed image by mixing the medical image before the denoise is performed and the denoise image on which the denoise has been performed according to the determined mixing rates. Accordingly, it is possible to generate a medical image which can further improve diagnosis accuracy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. A medical information processing apparatus, comprising:
processing circuitry configured to
acquire first data generated as a result of a reception by a radio frequency coil and acquire information about reception characteristics of the radio frequency coil that contribute to a signal-to-noise ratio of the first data;
perform a denoise process on the first data to obtain second data from the first data, the second data being the denoised first data;
determine multiple mixing rates based on the reception characteristics of the radio frequency coil, each mixing rate being a rate of a mixture of a first medical image according to the first data and a second medical image according to the second data; and
generate a mixed image by mixing the first medical image and the second medical image according to the determined multiple mixing rates,
wherein the processing circuitry is further configured to generate the mixed image by mixing the first medical image and the second medical image according to the mixing rates based on the information about reception characteristics of the radio frequency coil.

2. The medical information processing apparatus according to claim 1, wherein the acquired information about the reception characteristics of the radio frequency coil includes a g-factor map.

3. The medical information processing apparatus according to claim 1, wherein the processing circuitry is further configured to
generate a third map with which the multiple mixing rates that differ according to positions are associated, based on the information about reception characteristics of the radio frequency coil;
multiply the respective pixel values of the first medical image and the second medical image by the mixing rates based on the generated third map; and
generate the mixed image by summing the medical images having the pixel values multiplied by the mixing rates.

4. The medical information processing apparatus according to claim 1, wherein the processing circuitry is further configured to
acquire a g-factor map as the acquired information;
multiply the respective pixel values of the first medical image and the second medical image by the mixing rates based on multiple g-factors included in the g-factor map; and
generate the mixed image by summing the medical images having the pixel values multiplied by the mixing rates.

5. The medical information processing apparatus according to claim 4, wherein the processing circuitry is further configured to
generate a third map with which the mixing rates that differ according to positions are associated based on the g-factor map; and
multiply the respective pixel values of the first medical image and the second medical image by the mixing rates based on the third map.

6. The medical information processing apparatus according to claim 1, wherein the information about the reception characteristics of the radio frequency coil includes information of a reception sensitivity.

7. The medical information processing apparatus according to claim 1, wherein the processing circuitry is further configured to:
acquire a reception sensitivity map as the acquired information;
multiply the respective pixel values of the first medical image and the second medical image by the mixing rates based on multiple reception sensitivities included in the reception sensitivity map; and
generate the mixed image by summing the medical images having the pixel values multiplied by the mixing rates.

8. The medical information processing apparatus according to claim 7, wherein the processing circuitry is further configured to:
generate a third map with which the mixing rates that differ according to positions are associated based on the reception sensitivity map; and
multiply the respective pixel values of the first medical image and the second medical image by the mixing rates based on the third map.

9. The medical information processing apparatus according to claim 1, wherein the processing circuitry is further configured to perform the denoise process on the first data to obtain second data from the first data by a trained denoise model, the second data being the denoised first data.

10. The medical information processing apparatus according to claim 9, wherein the trained denoise model includes one or more deep neural networks.

11. A medical information processing apparatus, comprising:
processing circuitry configured to
acquire first data generated as a result of a reception by a radio frequency coil and acquire information about reception characteristics of the radio frequency coil that contribute to a signal-to-noise ratio of the first data;
perform a denoise process on the first data to obtain second data from the first data, the second data being the denoised first data;
select a mixing rate from multiple mixing rates, each mixing rates being a rate of a mixture of a first medical image according to the first data and a second medical image according to the second data; and
generate the mixed image by mixing the first medical image and the second medical image according to the selected mixing rate.

12. The medical information processing apparatus according to claim 11, wherein the processing circuitry is further configured to perform the denoise process on the first data to obtain second data from the first data by a trained denoise model, the second data being the denoised first data.

13. The medical information processing apparatus according to claim 12, wherein the trained denoise model includes one or more deep neural networks.

* * * * *